(12) United States Patent
Koblish

(10) Patent No.: US 7,938,828 B2
(45) Date of Patent: May 10, 2011

(54) COOLED ABLATION CATHETER

(75) Inventor: Josef V. Koblish, Palo Alto, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 317 days.

(21) Appl. No.: 10/402,891

(22) Filed: Mar. 28, 2003

(65) Prior Publication Data
US 2004/0193149 A1    Sep. 30, 2004

(51) Int. Cl.
*A61B 18/18* (2006.01)
(52) U.S. Cl. .............................. 606/49; 606/41; 606/59
(58) Field of Classification Search .............. 606/41–50; 607/101, 102, 104–106, 113, 116
See application file for complete search history.

(56) References Cited

U.S. PATENT DOCUMENTS

| | | | |
|---|---|---|---|
| 4,674,499 A | 6/1987 | Pao | |
| 4,685,459 A | 8/1987 | Koch et al. | |
| 4,805,616 A | 2/1989 | Pao | |
| 4,860,744 A | 8/1989 | Johnson et al. | |
| 4,896,671 A | 1/1990 | Cunningham et al. | |
| 4,955,377 A | 9/1990 | Lennox et al. | |
| 5,007,908 A | 4/1991 | Rydell | |
| 5,083,565 A | 1/1992 | Parins | |
| 5,139,496 A | 8/1992 | Hed | |
| 5,207,674 A | 5/1993 | Hamilton | |
| 5,230,349 A | 7/1993 | Langberg | |
| 5,254,088 A | 10/1993 | Lundquist et al. | |
| 5,273,535 A | 12/1993 | Edwards et al. | |
| 5,279,569 A | 1/1994 | Neer et al. | |
| 5,281,213 A | 1/1994 | Milder et al. | |
| 5,281,215 A | 1/1994 | Milder | |
| 5,281,217 A | 1/1994 | Edwards et al. | |
| 5,330,466 A | 7/1994 | Imran | |
| 5,334,145 A | 8/1994 | Lundquist et al. | |
| 5,334,193 A | 8/1994 | Nardella | |
| 5,336,182 A * | 8/1994 | Lundquist et al. ............ 604/528 |
| 5,336,222 A | 8/1994 | Durgin, Jr. et al. | |
| 5,348,554 A | 9/1994 | Imran et al. | |
| 5,391,199 A | 2/1995 | Ben-Haim | |
| 5,397,304 A * | 3/1995 | Truckai ........................ 604/528 |
| 5,423,807 A | 6/1995 | Milder | |
| 5,423,811 A | 6/1995 | Imran et al. | |
| 5,431,649 A | 7/1995 | Mulier et al. | |

(Continued)

OTHER PUBLICATIONS

PCT International Search Report for PCT/US04/008002, Applicant: Scimed Life Systems, Inc., Forms PCT/ISA/210 and 220, dated Aug. 11, 2004 (8 pages).

(Continued)

*Primary Examiner* — Roy D Gibson
(74) *Attorney, Agent, or Firm* — Vista IP Law Group LLP

(57) ABSTRACT

Steerable catheter that has fluid transfer capability is provided. The catheter includes an elongate flexible shaft having a proximal end and a distal end, an operative element carried at the distal end of the shaft, and a medium conveying conduit carried within the elongate shaft, the conduit having a distal end that is affixed relative to the distal end of the elongate shaft, and a proximal end that is configured to move relative to the proximal end of the shaft. In this manner, the proximal end of the medium conveying conduit is allowed to slide relative to the proximal end of the shaft as the distal end of the shaft changes shape, thereby preventing kinking of the conduit.

67 Claims, 10 Drawing Sheets

U.S. PATENT DOCUMENTS

| | | | |
|---|---|---|---|
| 5,433,198 A | 7/1995 | Desai | |
| 5,529,067 A | 6/1996 | Larsen et al. | |
| 5,540,679 A | 7/1996 | Fram et al. | |
| 5,545,161 A | 8/1996 | Imran | |
| 5,607,462 A | 3/1997 | Imran | |
| 5,658,278 A | 8/1997 | Imran et al. | |
| 5,676,693 A | 10/1997 | LaFontaine | |
| 5,697,927 A | 12/1997 | Imran et al. | |
| 5,800,432 A | 9/1998 | Swanson | |
| 5,800,484 A | 9/1998 | Gough et al. | |
| 5,840,031 A | 11/1998 | Crowley | |
| 5,876,373 A * | 3/1999 | Giba et al. | 604/95.04 |
| 5,921,982 A * | 7/1999 | Lesh et al. | 606/41 |
| 5,961,513 A | 10/1999 | Swanson et al. | |
| 6,030,379 A | 2/2000 | Panescu et al. | |
| 6,032,077 A | 2/2000 | Pomeranz | |
| 6,033,378 A | 3/2000 | Lundquist et al. | |
| 6,053,912 A | 4/2000 | Panescu et al. | |
| 6,056,744 A | 5/2000 | Edwards | |
| 6,056,745 A | 5/2000 | Panescu et al. | |
| 6,068,653 A * | 5/2000 | LaFontaine | 607/116 |
| 6,071,278 A | 6/2000 | Panescu et al. | |
| 6,080,151 A | 6/2000 | Swartz et al. | |
| 6,112,123 A | 8/2000 | Kelleher et al. | |
| 6,113,591 A | 9/2000 | Whayne et al. | |
| 6,123,084 A * | 9/2000 | Jandak et al. | 128/898 |
| 6,315,776 B1 | 11/2001 | Baker et al. | |
| 6,471,697 B1 | 10/2002 | Lesh | |
| 6,485,455 B1 | 11/2002 | Thompson et al. | |
| 6,506,189 B1 | 1/2003 | Rittman, III et al. | |
| 6,522,930 B1 | 2/2003 | Schaer et al. | |
| 6,837,885 B2 * | 1/2005 | Koblish et al. | 606/41 |
| 7,276,061 B2 * | 10/2007 | Schaer et al. | 607/41 |
| 2002/0103519 A1 * | 8/2002 | Dobak et al. | 607/105 |
| 2004/0093044 A1 * | 5/2004 | Rychnovsky et al. | 607/88 |

OTHER PUBLICATIONS

PCT Written Opinion of the International Search Authority for PCT/US04/008002, Applicant Scimed Life Systems, Inc., Form PCT/ISA/237, dated Aug. 11, 2004 (6 pages).

* cited by examiner

LESION VOLUME INCREASE
vs.
ELECTRODE TEMPERATURE
(MAXIMUM TISSUE TEMPERATURE AT 94°C)

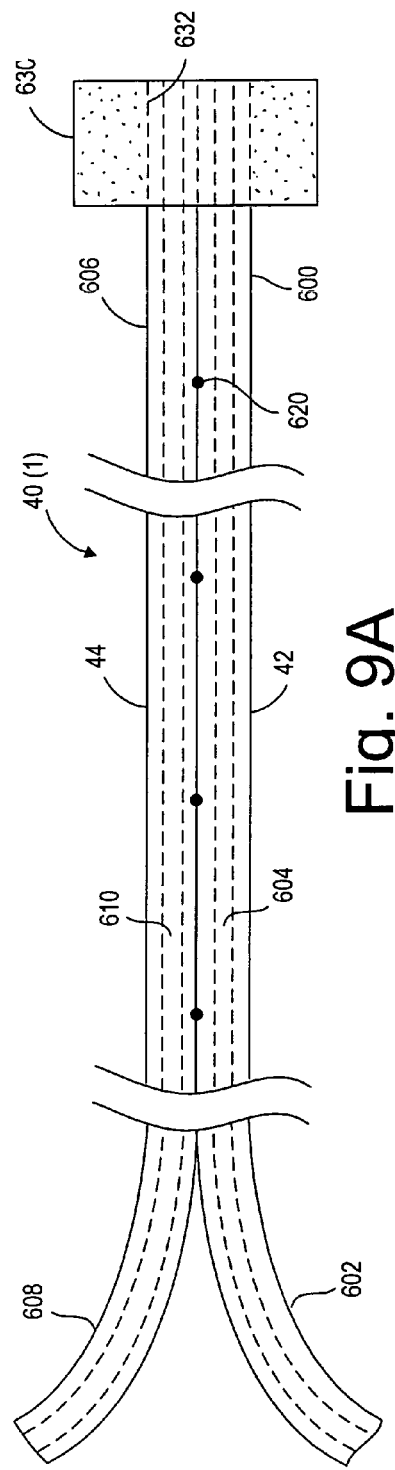
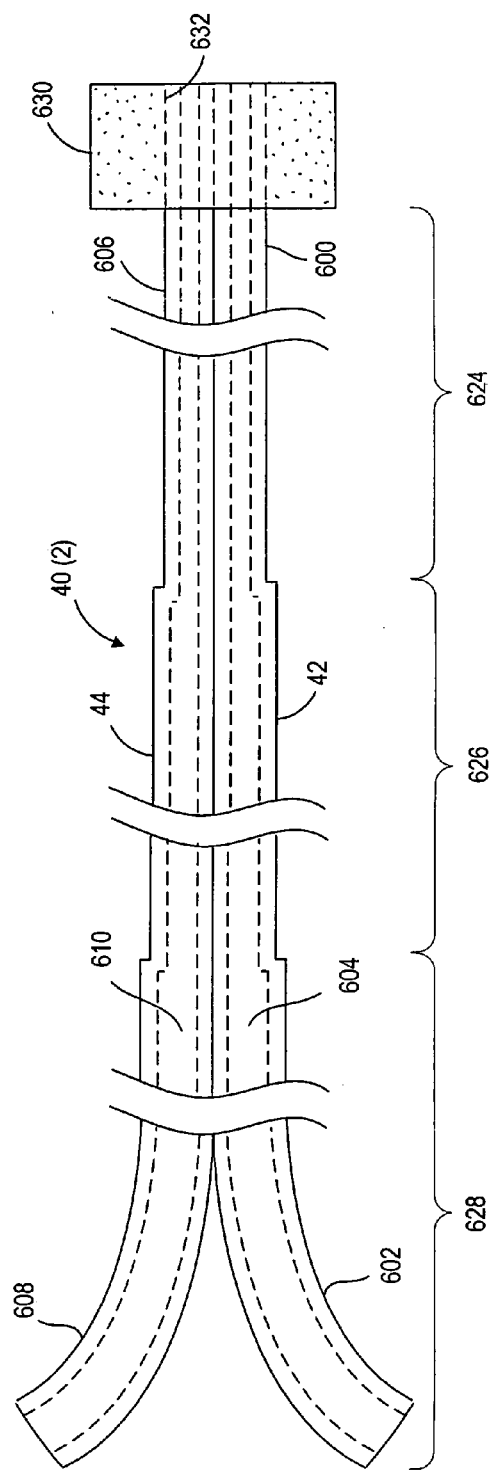
Fig. 9A
Fig. 9B

COOLED ABLATION CATHETER

FIELD OF THE INVENTION

The present invention pertains to devices and methods for treating tissue, and more particularly, to ablation devices and methods for creating lesions on tissue.

BACKGROUND

Physicians make use of catheters today in medical procedures to gain access into interior regions of the body to ablate targeted tissue areas. For example, in electrophysiological therapy, ablation is used to treat cardiac rhythm disturbances. During these procedures, a physician steers a catheter through a main vein or artery into the interior region of the heart that is to be treated. The physician places an ablating element carried on the catheter near the cardiac tissue that is to be ablated. The physician directs energy from the ablating element to ablate the tissue and form a lesion. Such procedure may be used to treat atrial fibrillation, a condition in the heart in which abnormal electrical signals are generated in the endocardial tissue.

Ablation catheters typically have an elongated shaft carrying an electrode at its distal end. Lesions of different shapes and sizes may be formed by choosing a suitable electrode shape or size, and/or by manipulating the position of the electrode at the distal end of the catheter. An ablation catheter may also have a steering mechanism for steering its distal end, which is beneficial because it allows a physician to steer the catheter through veins and vessel junctions. It also allows the physician to accurately position the electrode carried at the distal end at a target site to be ablated. Steerable ablation catheters have been described in U.S. Pat. Nos. 6,033,378 and 6,485,455 B1, the disclosures of which are expressly incorporated by reference herein.

Torquable catheters have also been described in U.S. patent application Ser. No. 07/657,106, filed Feb. 15, 1991, the disclosure of which is hereby incorporated by reference in its entirety. Such a catheter provides a torsional stiffness such that when a physician applies a torque at a handle at the proximal end of the catheter, a corresponding torquing force is transmitted to the distal end of the catheter. This transmitted torquing force allows the physician to press the electrode against a tissue surface by torquing the distal end of the catheter.

During use of an ablation catheter, the electrode delivering ablation energy may overheat, thereby causing tissue charring and preventing formation of a deeper lesion. This may negatively affect the ablation catheter's ability to create a desirable lesion. An overheated electrode may also cause healthy tissue adjacent the target site to be heated. Furthermore, an overheated electrode may cause blood to be heated, thereby creating an undesirable embolism. As such, an ablation catheter that is capable of cooling an electrode is very desirable. Systems and methods for ablating tissue using actively cooled electrodes have been described in U.S. Pat. No. 5,800,432, the entire disclosure of which is expressly incorporated by reference herein.

Ablation catheters that have cooling capability may have a fluid delivery tube for delivering a cooling fluid to an electrode during use. If not designed or constructed properly, the fluid delivery tube may kink or buckle during use, especially if the ablation catheter has steering or torquing capability.

Thus, there is currently a need for an improved steerable/torquable ablation catheter that is capable of cooling an electrode tip during use, while preventing the fluid delivery lumen from kinking or buckling when the catheter is bent, e.g., during steering or torquing operations.

SUMMARY OF THE INVENTION

According to one aspect of the invention, a medical system includes a catheter and a cooling assembly. The catheter includes an elongate flexible shaft having a proximal end and a distal end, an operative element carried at the distal end of the shaft, and a medium conveying conduit carried within the elongate shaft, the conduit having a distal end that is affixed relative to the distal end of the elongate shaft, and a proximal end that is configured to move relative to the proximal end of the shaft. The catheter may also include a steering mechanism for steering the distal end of the catheter. The cooling assembly includes a source reservoir coupled to the medium conveying conduit.

According to another aspect of the invention, a catheter includes an elongate flexible shaft having a proximal end and a distal end, an operative element carried at the distal end of the shaft, and a first medium conveying conduit carried within the elongate shaft, the first conduit having a distal end, a proximal end, and a lumen extending between the distal end proximal ends, the lumen having a first cross-sectional size at a first location along the length of the first conduit, and a second cross-sectional size at a second location along the length of the first conduit. The catheter may further include additional medium conveying conduit(s). In one embodiment, the lumen of the first medium conveying conduit has a cross section that varies continuously between the first location and the second location along the length of the first conduit. In another embodiment, the lumen of the first medium conveying conduit changes from its first cross-sectional size to its second cross-sectional size at a discrete location between the first location and the second location along the length of the first conduit.

In one embodiment, the catheter is used to ablate tissue. In another embodiment, the catheter may be used for delivery of a drug or contrast agent. In yet another embodiment, the catheter may be used for removing objects or fluid from a site. In this case, instead of a cooling assembly, a suction generator is coupled to the proximal end of the catheter.

Other and further aspects and features of the invention will be evident from reading the following detailed description of the drawings, which is intended to illustrate, not limit, the invention.

BRIEF DESCRIPTION OF THE DRAWINGS

Preferred embodiments of the present invention are illustrated by way of example, and not by way of limitation, in the figures of the accompanying drawings, in which like reference numerals refer to like components, and in which:

FIG. 9A is a top view of an embodiment of a fluid transfer assembly used in the catheter of FIG. 3;

FIG. 9B is a top view of an alternative embodiment of a fluid transfer assembly used in the catheter of FIG. 3;

DESCRIPTION OF THE PREFERRED EMBODIMENTS

Figure 1:
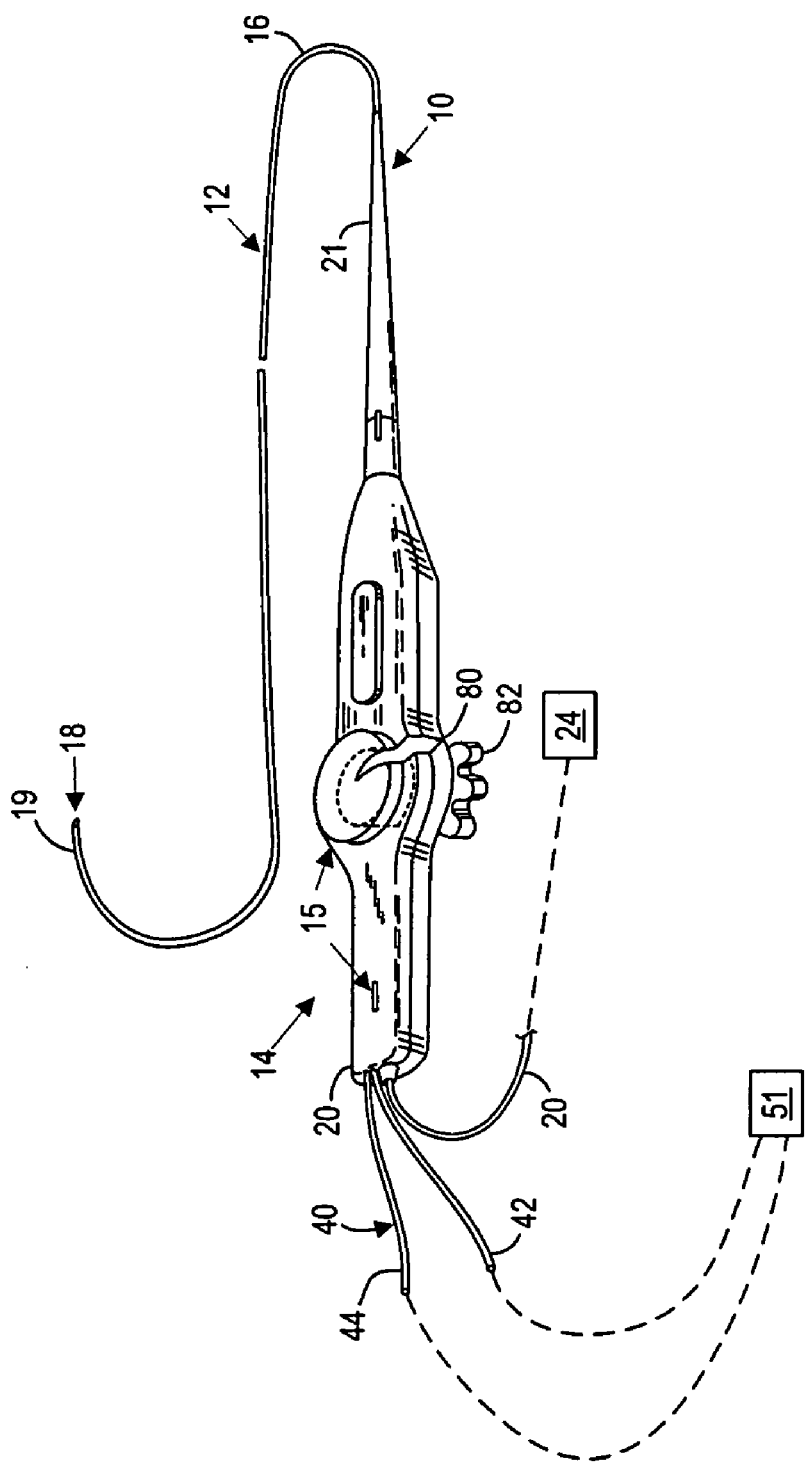
FIG. 1 is a perspective view of a system that embodies the features of the invention.

Referring to FIG. 1, a tissue ablation system 10 constructed in accordance with one preferred embodiment of the present invention is shown. The system 10 generally includes an ablation catheter 12, a generator 24 for delivering ablation energy to the catheter 12 to ablate target tissue, and a cooling assembly 51 for delivering a cooling medium to the catheter 12, thereby promoting efficient and safer ablation of the target tissue.

The catheter 12 comprises three main parts or assemblies: a handle assembly 14, a guide tube assembly 16, and an electrode tip assembly 18, the details of which will be discussed further below.

The generator 24 is coupled to the handle assembly 12 of the catheter 12 via a cable 20, so that RF energy can be delivered to the electrode assembly 18. In the illustrated and preferred embodiment, the generator 24 is a radio frequency (RF) generator that delivers RF energy to ablate tissue. However, other types of energy, e.g., laser energy, may also be used for tissue ablating purposes. In the illustrated embodiment, the system 10 operates in a unipolar mode. In this arrangement, the generator 24 may include an indifferent patch electrode (not shown) that attaches to the patient's back or other exterior skin area. In this case, ablation energy will flow from the electrode tip assembly 18 to the patch electrode. Alternatively, the system 10 can be operated in a bipolar mode, in which case, ablation energy will flow from one electrode on the electrode tip assembly 18 to an adjacent electrode on the electrode tip assembly 18.

The cooling assembly 51 is configured for actively cooling the electrode tip assembly 18. Specifically, the cooling assembly 51 is configured for supplying a cooling fluid to the catheter 12, and carrying heated cooling fluid from the catheter 12.

Figure 1A:
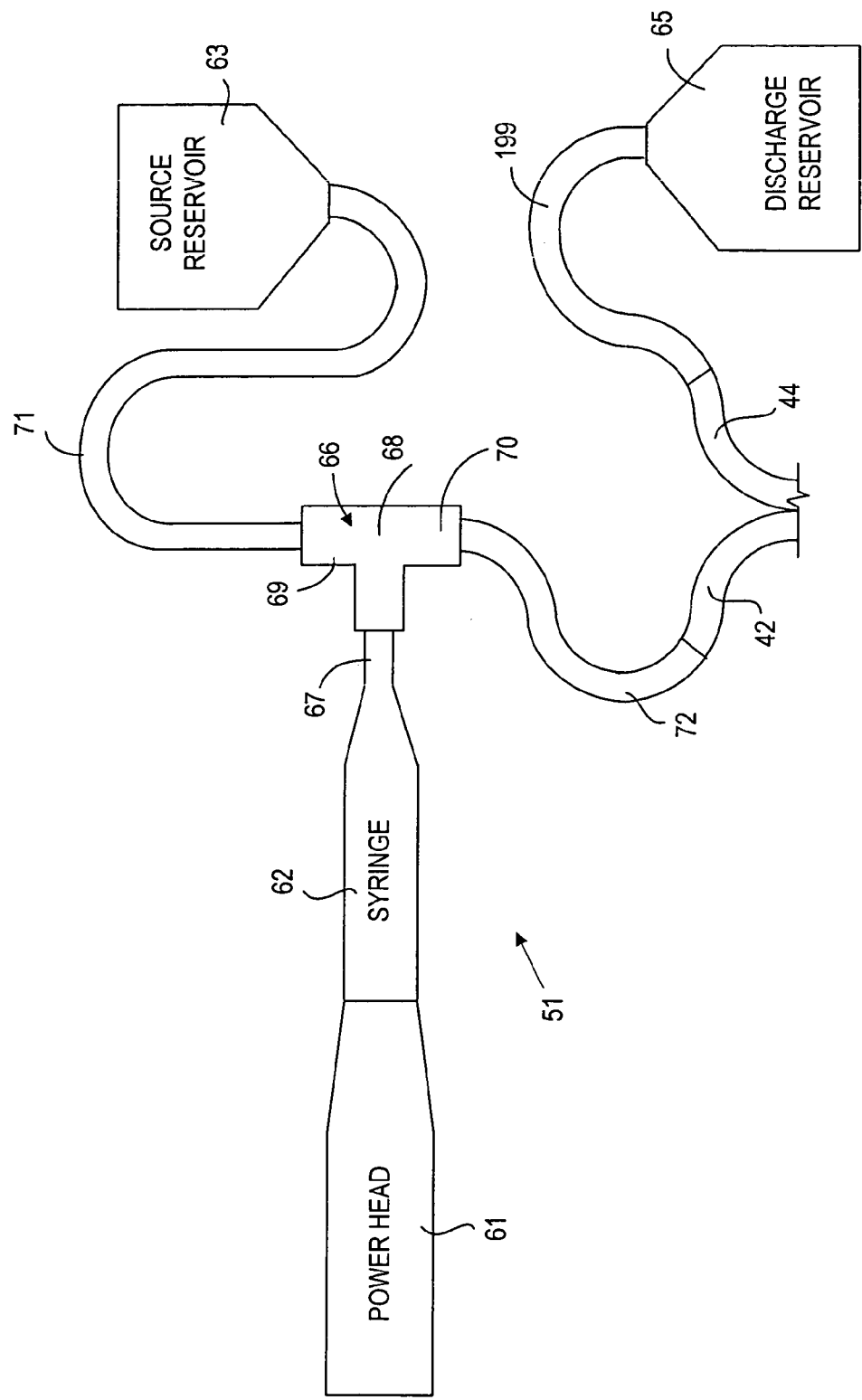
FIG. 1A is a block diagram of an example of a pump assembly shown in the system of FIG. 1.

Referring to FIG. 1A, the details of the cooling assembly 51 will be described. The cooling assembly 51 comprises a power head 61 and a syringe 62 that is front-loaded on the power head 61 and is of a suitable size, e.g., 200 ml. The power head 61 and the syringe 62 are conventional and can be of the type described in U.S. Pat. No. 5,279,569 and supplied by Liebel-Flarsheim Company of Cincinnati, Ohio. The cooling assembly 51 further comprises a source reservoir 63 for supplying the cooling medium to the syringe 62, and a discharge reservoir 65 for collecting the heated medium from electrode assembly 18. The cooling assembly 51 further comprises a tube set 66 removably secured to an outlet 67 of the syringe 62. Specifically, a dual check valve 68 is provided with first and second legs 69 and 70, of which the first leg 69 serves as a liquid inlet connected by tubing 71 to the source reservoir 63. The second leg 70 is an outlet leg and is connected by tubing 72 to catheter 12 via tube 42. The discharge reservoir 65 is connected to the catheter 12 via tube 44. The tubes 42 and 44 will be described in further details.

Alternatively, the cooling assembly 40 does not include a pump 50, but rather conveys a cooled medium to the catheter 12 via other means, e.g., gravity. The cooling assembly 40 may further include a cooling device (not shown) for cooling the medium. Alternatively, if the cooled medium is pre-cooled or need not be cooled, e.g., the cooled medium at room temperature is sufficient, then the cooling device is optional. In one embodiment, if active cooling is desired, the cooling assembly 40 may further include a controller (not shown) for controlling the rate of cooling. An example of such a controller is described in U.S. Pat. No. 5,800,432.

Thus, it can be appreciated that the cooling assembly 51 can be operated to periodically fill the syringe 62 with the cooling medium from the source reservoir 63, and convey the cooling medium from the syringe 62, through the tubing 72, and into the lumen of the tube 42. Heated medium is conveyed from the lumen of the tube 44, through the tubing 73, and into the collection reservoir 65. The cooling assembly 51, along with the RF generator 24, can include control circuitry to automate or semi-automate the cooled ablation process.

Figure 2A:
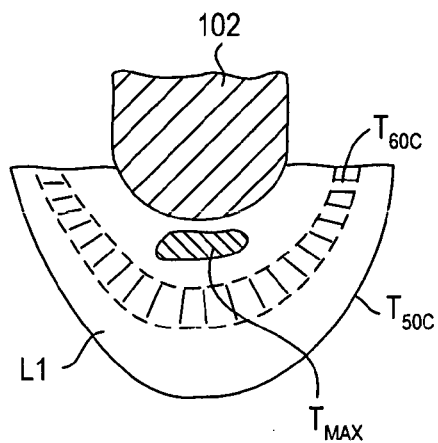
FIG. 2A is a diagrammatic view of a lesion profile, without an actively cooled ablation electrode.
Figure 2B:
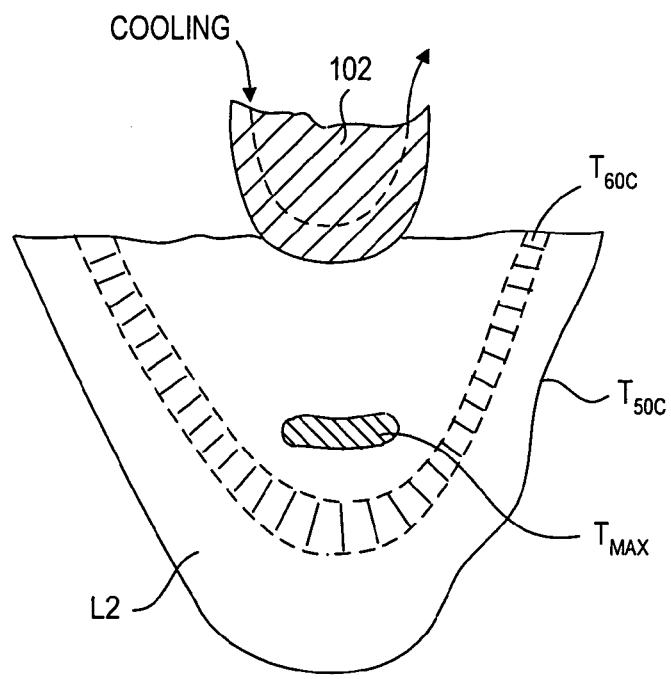
FIG. 2B is a diagrammatic view of a lesion profile, with an actively cooled ablation electrode.
Figure 2C:
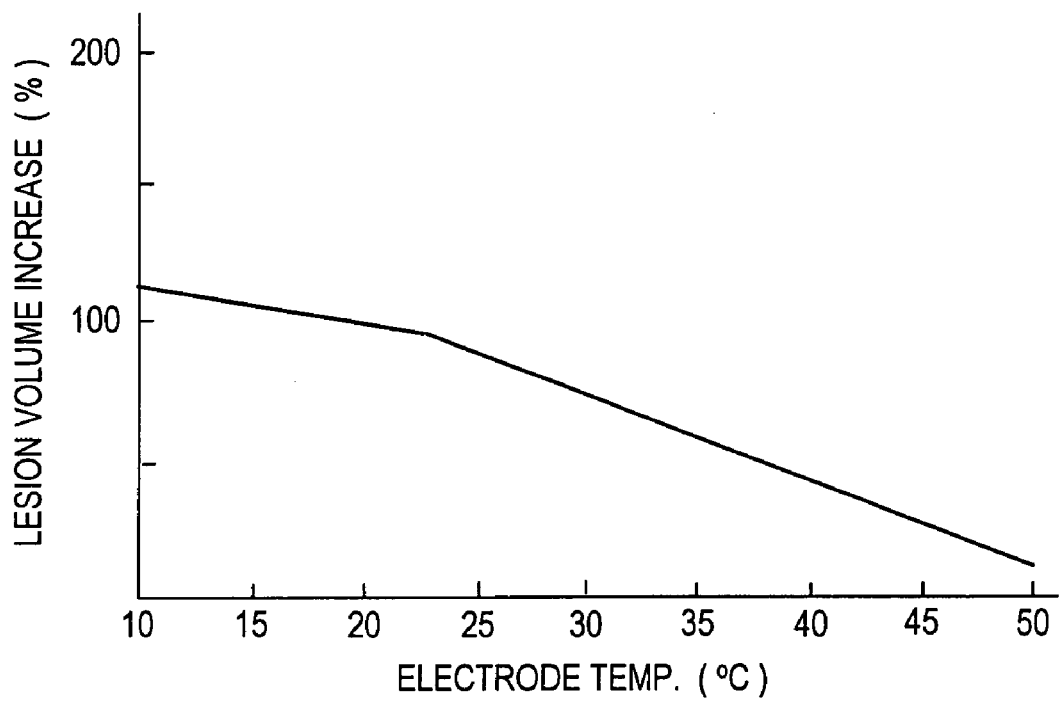
FIG. 2C is a graph showing the increase in lesion volume as a function of the cooling temperature of the ablation electrode.

Cooling causes the electrode-tissue interface to have lower temperature values. As a result (as FIGS. 2A and 2B show), the hottest iso-thermal region $T_{MAX}$ is shifted deeper into the tissue. This, in turn, shifts the 50° C. iso-thermal region (designated $T_{50C}$), which determines the boundary of the tissue rendered nonviable by ablation, deeper into the tissue. An electrode that is actively cooled can be used to transmit more ablation energy into the tissue, compared to the same electrode that is not actively cooled. As a comparison of FIGS. 2A and 2B shows, the net result is that, with cooling, the lesion (designated L1 and L2, respectively, in FIGS. 2A and 2B) extends deeper into the tissue and has a larger volume. FIG. 2C shows this effect graphically. Assuming a maximum tissue temperature $T_{MAX}$ of about 94° C., actively cooling the electrode to an electrode temperature $T_1$ below about 35° C. leads to at least a 50% increase in lesion volume. At an electrode temperature $T_1$ below about 25° C., lesion volumes increase by about 100%, i.e., lesion volumes double in size.

Figure 3:
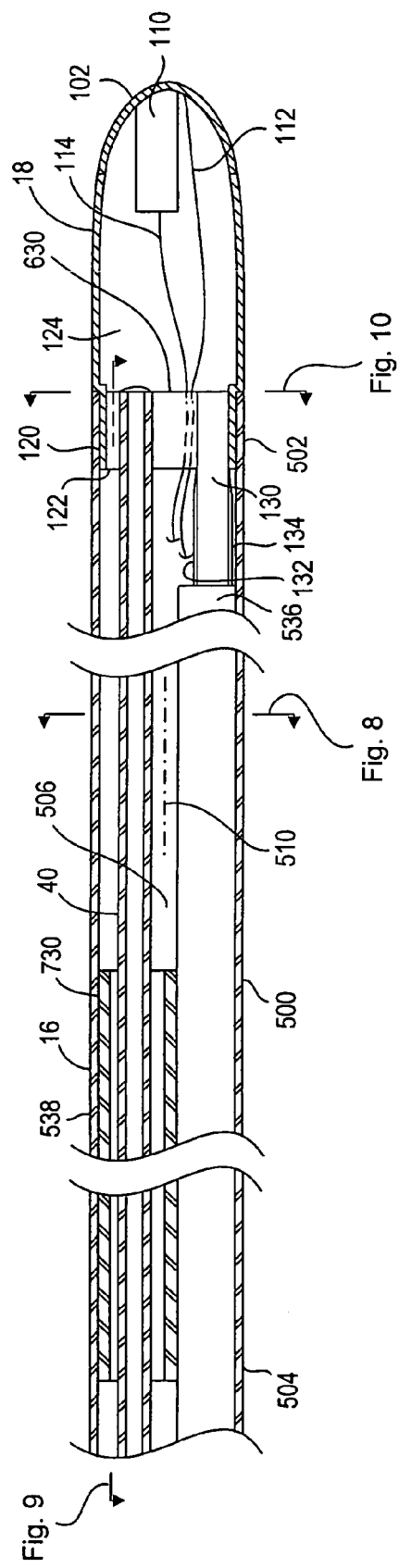
FIG. 3 is a partial side cross-sectional view of an embodiment of a catheter used in the system of FIG. 1.

Turning now to FIG. 3, the details of the catheter 12 will be described. As shown, the electrode assembly 18 comprises a tip electrode 102 located at the distal end of the guide tube assembly 16 and an optional temperature sensing element 110, such as a thermocouple or thermistor, secured adjacent to the tip electrode 102. Although the tip electrode 102 has a circular cross section in the illustrated embodiment, the tip electrode 102 may have other cross-sectional shapes, such as elliptical, rectangle, or other designed shapes. In alternative embodiments, the electrode assembly 18 may comprise multiple electrodes, e.g., electrodes that extend along the distal end of the guide tube assembly 16 in a segmented fashion. The electrode 102 is composed of a suitably thermal conductive biocompatible material, such as, e.g., platinum/iridium, stainless steel, gold, or silver. The electrode assembly 18 also includes an ablation wire 112 connected to the electrode 102, and a signal wire 114 connected to the sensing element 110. The ablation wire 112 can optionally be used to transmit signals to and from the electrode 102, e.g., during an electrophysiology mapping function.

The proximal end 120 of the electrode assembly 18 has an opening 122, which is in fluid communication with an interior 124 of the tip electrode 102. In the illustrated embodiment, the interior 124 is entirely closed, thereby allowing the electrode assembly 18 to contain fluid delivered through the opening 122. Such configuration of the electrode assembly 18 is suitable for closed loop cooling. Closed loop cooling, and devices for performing such functions, have been described in U.S. Pat. No. 5,800,432, as previously mentioned herein.

Referring back to FIG. 1, the handle assembly 14 includes a handle 22 for grasping by the physician and a steering mechanism 15 for steering the electrode tip assembly 18. The steering mechanism 15 includes a steering lever 80 and a locking lever 82. The steering lever 80 is operable for steering of the electrode tip, and the locking lever 82 is operable in a first position to lock the steering lever 80 in place, and in a second position to release the steering lever 80 from a locked configuration. As illustrated in FIG. 3, the steering mechanism 15 further comprises a spring element 130, which is secured at the proximal end 120 of the electrode assembly 18, and left and right steering wires 132 and 134, which are secured to the opposite sides of the spring element 130. Alternatively, a single steering wire is secured to one side of the spring element 130. Also, in another embodiment, the spring element may be secured to the distal end of the guide tube assembly 16 proximal to the electrode assembly 18.

Figure 4:
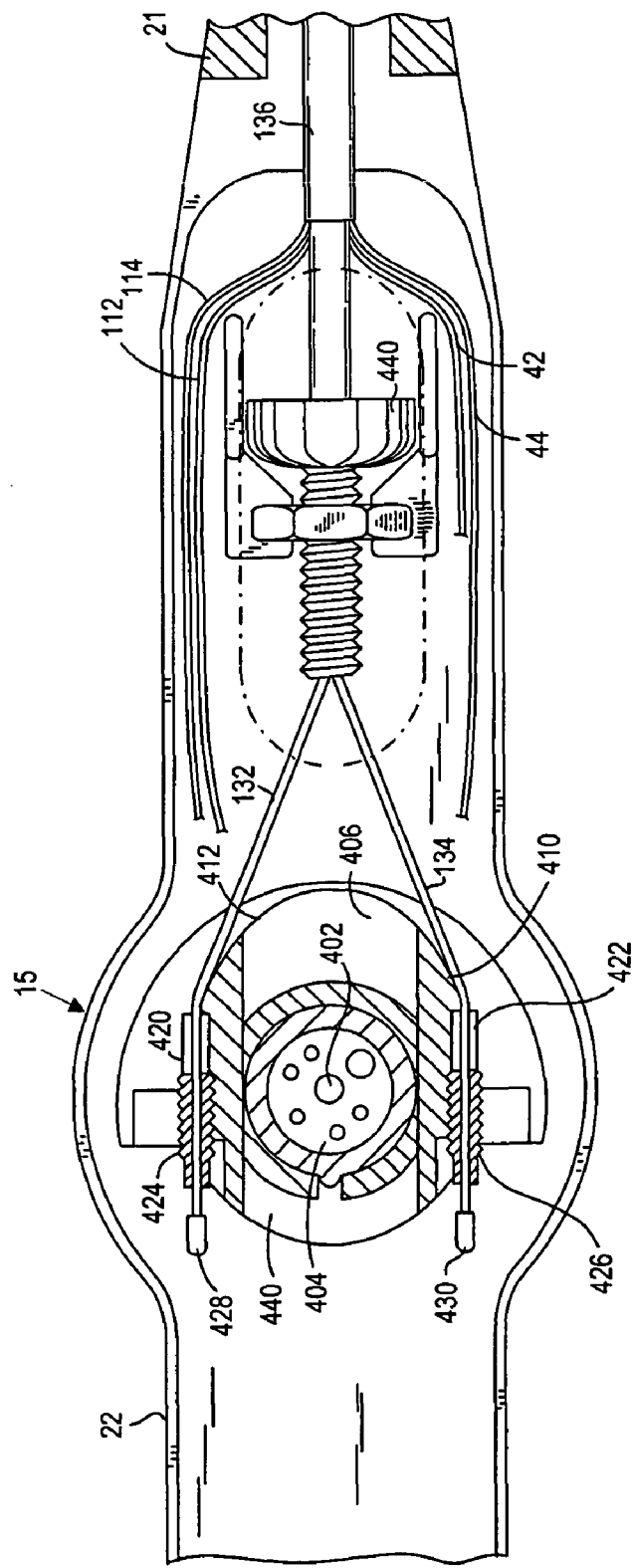
FIG. 4 is a partial cut-away view of the handle assembly of the catheter shown in the system of FIG. 1.
Figure 5:
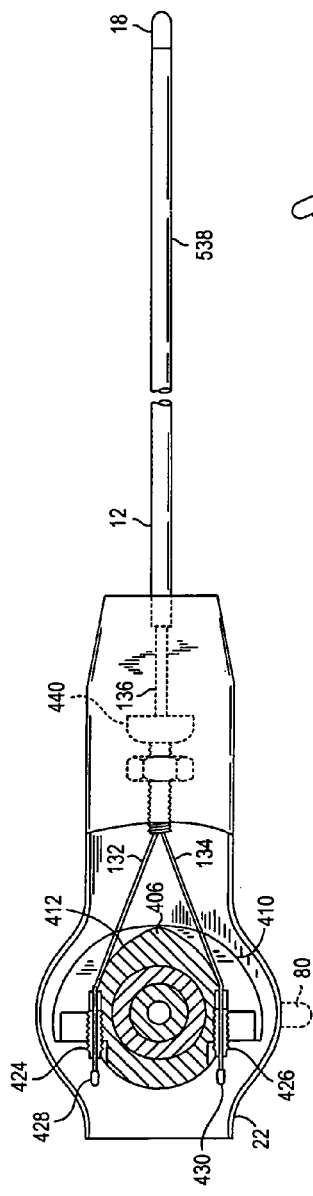
FIG. 5 is a partial cut-away view of the catheter shown in the system of FIG. 1 in a relaxed position.

The handle assembly 14 will now described in further detail with reference to FIGS. 4-7. As shown in FIGS. 4 and 5, the steering mechanism 15 includes a rotatable cam 400 carried on a screw 402 within the handle 22. The rotatable cam 400 is seated for rotation between a top washer 404 and a bottom washer (not shown). The screw 402 is threaded into a central opening in the washer 404. The external steering lever 80 is adhesively bonded or ultrasonically welded to the top of the rotatable cam 400. The steering lever 80 also seats against an O-ring (not shown). Further details regarded the O-rings and similar assembly details are described in U.S. Pat. No. 5,273,535, the entire disclosure of which is herein incorporated by reference.

The rotatable cam 400 includes a forward cam face 406. The forward cam face 406 includes a right side cam surface 410 and a left side cam surface 412. The surfaces 410 and 412 are located at the bottoms of grooves in the lateral edges of the rotatable cam 400. The surfaces 410 and 412 may either be of the same (symmetric) radii or may be asymmetrically shaped. The rotatable cam 400 is provided on its lateral edges with threaded holes 420 and 422 into which adjustable stops 424 and 426, respectively, are threaded. The proximal ends of the catheter steering wires 132 and 134, pass through central openings in stops 424 and 426 and are attached to steering wire terminals 428 and 430, respectively.

The steering wires 132 and 134 extend from the stops 424 and 426 along the associated left and right side surfaces 412 and 410 of the cam face 406. The steering wires 132 and 134 exit the front of the housing 22 through the interior bore of a tension screw assembly 440, and extend from the tension screw assembly 440 through the guide tube assembly 16 to the electrode assembly 18. As discussed previously with reference to FIG. 3, the steering wires 132 and 134 are secured to the left and right sides of the spring element 130 at the distal end of the catheter 12.

Figure 6:
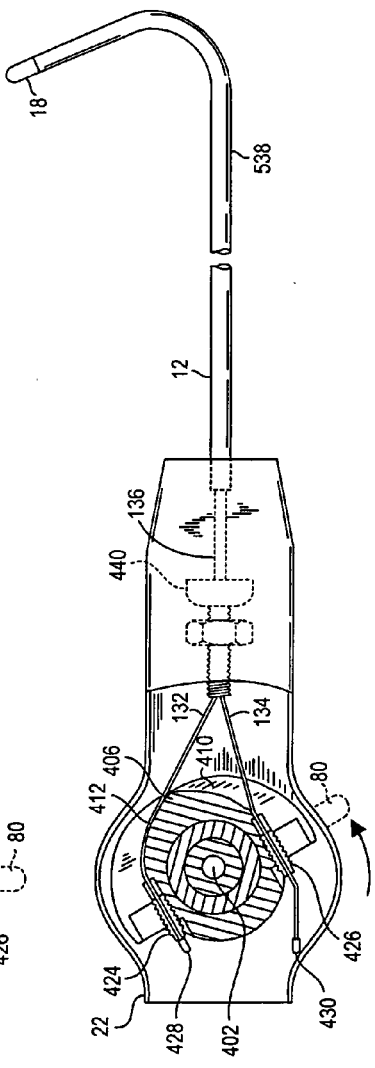
FIG. 6 is a partial cut-away view of the catheter of FIG. 5 steered to the left.
Figure 7:
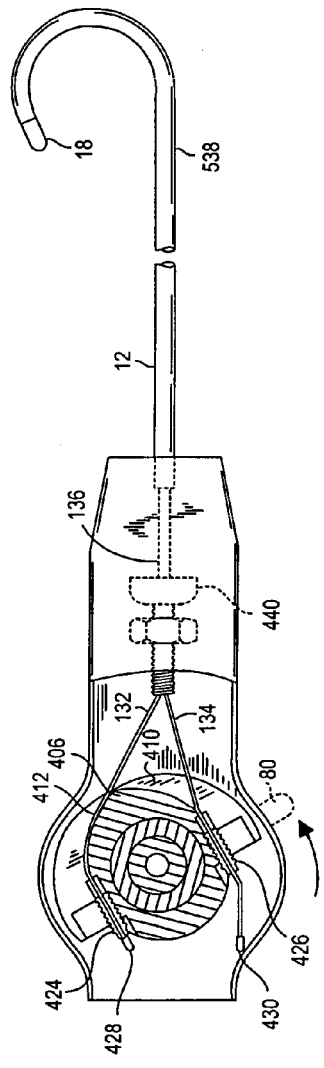
FIG. 7 is a partial cut-away view of the catheter of FIG. 5 with the steering mechanism adjusted to a different setting and steered to the left with a different curvature.

Movement of the steering lever 80 by the user rotates the rotatable cam 400 about the screw 402 within the housing 22. Clockwise movement of the steering level 80 rotates the rotatable cam 400 to the right. Counterclockwise movement of the steering wheel rotates the rotatable cam 400 to the left. By rotating the rotatable cam 400 to the left as shown in FIG. 6 (by moving the steering lever 80 counterclockwise), the left steering wire stop 424 bears against the left terminal block 428 and cam surface 412. This movement tensions the left steering wire 132 to impose a pulling force that causes the spring element 130, and therefore, ablation electrode 102, to bend to the left in a desired curvature. If a different degree of curvature is desired, for example, as shown in FIG. 7, stop 424 is rotated to extend it distally, thus adjusting the curvature as shown. If the cam surfaces 410 and 412 are asymmetric in shape, the range of possible curvatures is different for the right and left wires 132 and 134. Thus, a nearly infinite variety of curve shapes is possible by adjustment of the stops 424 and 426. By rotating the rotatable cam 400 to the right (by moving the steering lever 80 clockwise), tension is applied to the right steering wire 134 in the same manner as describe in connection with wire 132, causing the spring element 130, and therefore, the ablation electrode 102, to bend to the right. As such, by operating the steering lever 80, a physician can steer the ablation electrode 102 into contact with the tissue to be ablated.

It should be noted that the handle assembly 12 is not limited to the embodiment described previously, and that handles having other types of steering mechanisms may also be used. Further details regarding this and other types of handle assemblies can be found in U.S. Pat. Nos. 5,254,088, and 6,485,455 B1, the entire disclosures of which are hereby expressly incorporated by reference.

Referring back to FIG. 3, the guide tube assembly 16 includes a shaft 500 having a distal end 502 on which the electrode assembly 18 is mounted, a proximal end 504 on which the handle assembly 14 is secured, and a main lumen 506 extending between the distal and proximal ends 502 and 504. In the illustrated embodiment, the distal end 502 of the shaft 500 has a cross-sectional shape and dimension that are substantially the same as those for the tip electrode 102, thereby forming a substantially continuous surface with the electrode 102.

The shaft 500 is preferably made from a thermoplastic material, such as a polyurethane, a polyolefin or polyether-polyamide block copolymer. The shaft 500 may also be made from a variety of materials, such as polymer or plastics. In one embodiment, the shaft 500 includes a length of stainless steel coiled into a flexible spring, and a sheath of extruded plastic material containing wire braids enclosing the spring. Such construction provides additional torsional stiffness to the shaft 500, thereby allowing a torquing force to be transmitted from the handle assembly 14 to the electrode assembly 18 of the catheter 12. Alternatively, the shaft 500 may comprise a slotted, stainless steel tube. Further details of such slotted shafts are disclosed in U.S. patent application Ser. No. 07/657,106. The guide tube assembly 16 comprises an optional external sleeve 21 that is suitably bonded to the proximal end of the shaft 500 for enhancing the transmission of torque from the handle assembly 14 to the electrode tip assembly 18.

The guide tube assembly 16 further comprises an optional internal sleeve 536, such as, e.g., a Teflon® tube, for housing the spring element 130 and steering wires 132 and 134. In the preferred embodiment, the sleeve 536 is secured to an interior surface of the shaft 500. In this case, the sleeve 536 may be secured to the interior surface of the shaft 500 at a junction point 538 that is 2 to 6 inches from the distal end of the electrode assembly 18. The sleeve 536 may be secured to the shaft 500 at the junction point 538 by a suitable adhesive, or alternatively, be fused together with the shaft 500 at the junction point 538 by a heating or chemical process. Such construction provides additional torsional stiffness at the junction point 538, thereby allowing a torquing force to be transmitted from the handle assembly 14 to the distal portion of the catheter 12. Alternatively, the sleeve 536 may be secured to the interior surface of the shaft 500 at other position(s) or continuously along a length of the shaft 500.

The guide tube assembly 16 further comprises a fluid transfer assembly 40 that is configured for conveying the cooled medium from the pump assembly 51, and distally through the shaft 500 to the tip electrode 102, and conveying heated medium from the tip electrode 102 and proximally through the shaft 500 to the cooling assembly 51. To this end, the fluid transfer assembly 40 comprises the previously described first and second tubes 42 and 44, which are proximally connected to the pump assembly 51 (see FIG. 1) and distally connected to the tip electrode 102.

Figure 8A:
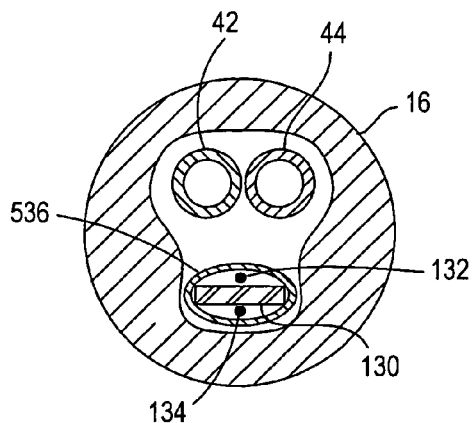
FIGS. 8A-8C are cross-sectional views of various embodiments of the catheter of FIG. 3 taken at lines 8-8.
Figure 8B:
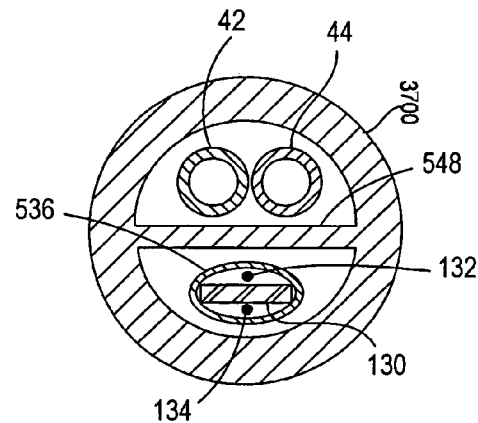
Figure 8C:
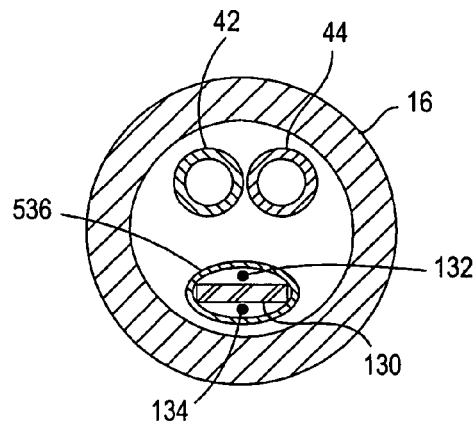

As shown in the illustrated embodiment, the fluid transfer assembly 40 together with the sleeve 536, are located within the lumen 506 of the shaft 500. In one embodiment, a distal portion of the shaft 500 proximal to the electrode assembly 18 has thickened wall section(s), such as that shown in FIG. 8A. Such a configuration allows the tubes 42 and 44 and the spring element 130 to be tightly packed within the shaft 500, and reduces the risk that either or both of the tubes 42 and 44 may twist around the spring element 130 or the sleeve 536 during use. Alternatively, the distal portion of the shaft 500 may have a uniform wall thickness at a cross section, and a dividing wall 548 dividing the lumen 506 into two spaces for housing the tubes 42 and 44 and the spring element 130, respectively (FIG. 8B). The wires 112 and 114 may be housed in either of the two spaces. In yet another embodiment, the shaft 500 may have a uniform wall thickness (FIG. 8C).

As shown in FIGS. 9A and 9B, the first tube 42 of the fluid transfer assembly 40 has a distal end 600, a proximal end 602, and a delivery lumen 604 extending between the distal and proximal ends 600 and 602. The second tube 44 also has a distal end 606, a proximal end 608, and a discharge lumen 610 extending between the distal and proximal ends 608 and 610. In the illustrated embodiment, the proximal ends 602 of the tube 42 is configured to couple to the source reservoir 63, while the proximal end 608 of the tube 44 is configured to couple to the discharge reservoir 65. The first and second tubes 42 and 44 are preferably composed of a polymer or a plastic, such as a 72 Durometer (D) PEBAX. In the illustrated embodiment, the walls of the respective first and second tubes 42 and 44 have a thickness within the range of 0.001" to 0.005". However, the walls of the first and second tubes 42 and 44 may also have other thickness as well. As shown in the illustrated embodiment, the lumens 604 and 610 of the respective tubes 42 and 44 are in fluid communication with the interior 124 of the tip electrode 102.

In one embodiment, the tubes 42 and 44 are secured to each other by a suitable adhesive at discrete points 620 along the lengths of the tubes 42 and 44. Alternatively, the tubes 42 and 44 may be secured to each other by a suitable adhesive that is substantially continuous along the lengths of the tubes 42 and 44. In another embodiment, the tubes 42 and 44 may also be fabricated or formed as one single unit during a manufacturing process. In yet another embodiment, the tubes 42 and 44 are not secured to each other along their lengths, but are only secured at their distal ends 600 and 606.

In one embodiment of the fluid transfer assembly 40(1) illustrated in FIG. 9A, the lumens 604 and 610 of the respective tubes 42 and 44 have a substantially uniform diameter along their lengths. In contrast, in another embodiment of the fluid transfer assembly 40(2) illustrated in FIG. 9B, the lumens 604 and 610 of the respective tubes 42 and 44 have a graduated diameter along their lengths. Specifically, the fluid transfer assembly 40(2) can be conceptually divided into a first portion 624, a second portion 626, and a third portion 628 along its length. The lumens 604 and 610 of the respective tubes 42 and 44 in the first portion 624 are smaller than those in the second portion 626 of the fluid transfer assembly 40. The lumens 604 and 610 of the respective tubes 42 and 44 in the second portion 626 are in turn, smaller than those in the third portion 628. Such a configuration is beneficial in that it reduces a head pressure within the tubes 42 and 44 for a given output by the pump 50. In one embodiment, the portions 624, 626, and 628 have respective cross sectional dimensions that are approximately 0.017 to 0.019 inch, 0.026 to 0.029 inch, and 0.035 to 0.040 inch, respectively. Although three portions 624, 626, and 628 are shown in the embodiment, alternatively, the fluid transfer assembly 40 may have two or more than three portions. In another embodiment, the exterior cross-sectional profiles of the tubes 42 and 44 are uniform along a substantial portion of their lengths, with their respective lumens 604 and 610 varying in size either at discrete location(s), or gradually, along their lengths.

Although the fluid transfer assembly 40 has been described as having two tubes 42 and 44, in other embodiments, the fluid transfer assembly 40 may also have more than two tubes for transferring fluid to and from the cooling assembly 51. Also, in an alternative embodiment, the fluid transfer assembly 40 has only a single tube for delivering a cooling fluid from the cooling assembly 51 to the electrode assembly 18 to perform open loop cooling. In this case, the cooling fluid is discharged at the electrode assembly 18, and the cooling assembly 51 does not include a discharge reservoir 65. Open and closed loop cooling will be described in further detail.

The fluid transfer assembly 40 also includes a plug 630 secured to the distal ends 600 and 606 of the respective tubes 42 and 44. In the illustrated embodiment, the plug 630 has a lumen 632 in which the distal ends 600 and 606 of the respective tubes 42 and 44 may be inserted and secured thereto using an adhesive. Alternatively, the plug 630 may be constructed such that the lumen 632 is slightly smaller than a cross-sectional dimension of the tubes 42 and 44, in which case, the tubes 42 and 44 are then frictionally secured within the lumen 632 of the plug 630. In yet another embodiment, the plug 630 and the tubes 42 and 44 may be made from the same material and are constructed or formed as a single unit during a manufacturing process.

Figure 10A:
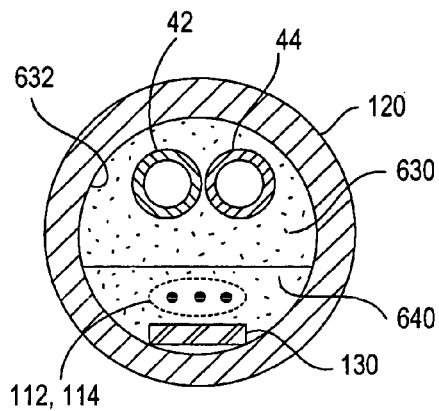
FIGS. 10A-10B are cross-sectional views of various embodiments of the catheter of FIG. 3 taken at lines 10-10.
Figure 10B:
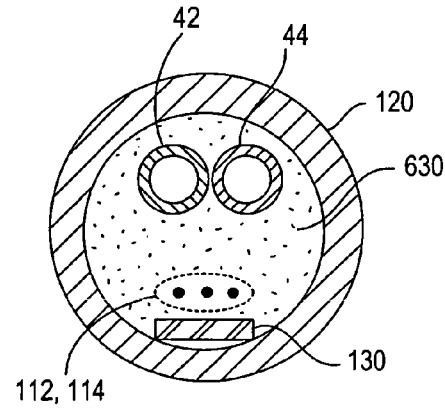

The plug 630 can be made from a variety of materials, such as polymer, rubber, plastic, Nylon, or metals. As shown in FIGS. 10A and 10B, the plug 630 has a shape and dimension such that it can be inserted into and mate with the opening 122 of the tip electrode 102. In one embodiment, the plug 630 is secured to the proximal end 120 of the electrode 102 by a glue, an epoxy, or a suitable adhesive. Alternatively, the plug 630 can be constructed to have a dimension that is slightly larger than the opening 122 of the electrode assembly 18, and the plug 630 can be frictionally secured to the electrode 102. Other techniques known in the art for securing a plug to an opening may also be used. In another embodiment, the plug 630 may be fabricated together with a portion of the electrode assembly 18, and the portion is then secured to the remaining portion of the electrode assembly 18.

In the embodiment shown in FIG. 10A, the plug 630 has a cross-section that resembles a "D" shape, and occupies a major portion of the opening 122. The unoccupied portion of the opening 122 accommodates the spring element 130 and the wires 112 and 114 that extend out of the opening 122 at the proximal end 120 of the electrode 102. A suitable filler 640 may be used to fill or plug the remaining unoccupied portion of the opening 122 so as to prevent fluid from escaping through the opening 122. In an alternative embodiment, such as that shown in FIG. 10B, the plug 630 may have a shape that substantially plugs the opening 122 without the use of the filler 640. In this case, the plug 630 has additional openings to accommodate the spring element 130 and the wires 112 and 114 that extend out of the opening 122 of the tip electrode 102. Furthermore, the shape of the plug 630 is not limited to that shown previously. In alternative embodiments, the plug 630 may have other shapes so long as it is capable of being secured to the tip electrode 102.

In the preferred embodiment, the proximal ends 602 and 608 of the tubes 42 and 44 of the fluid transfer assembly 40 are not affixed relative to the proximal end 504 of the shaft 500, while the distal ends 600 and 606 of the tubes 42 and 44 are affixed relative to the distal end 502 of the shaft 500, thereby allowing the tubes 42 and 44 to slide within the shaft 500 as the shaft 500 is bent. This has the benefit of allowing the tubes 42 and 44 to move correspondingly with the changing shape of the guide tube assembly 16 as the electrode assembly 18 is steered. The axial movement of the tubes 42 and 44 relative to the shaft 500 is due to the tubes 42 and 44 being offset (either because of design consideration, or because of manufacturing inconsistency) from a center line 510 of the shaft 500. This phenomenon is further explained with reference to FIGS. 11A-11C.

Figure 11B:
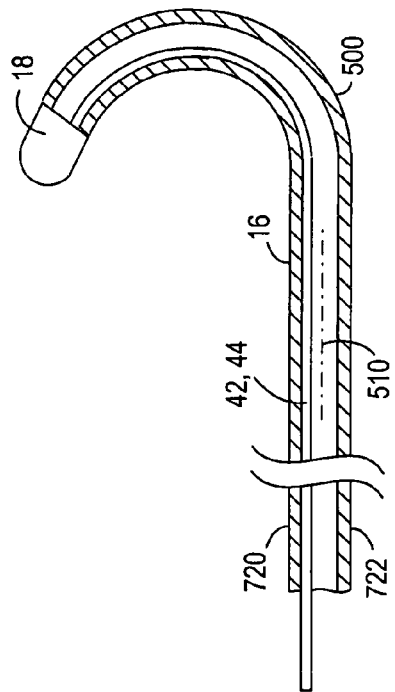
FIG. 11B is a cross-sectional view of a distal portion of the catheter of FIG. 3 steered to the left.
Figure 11A:
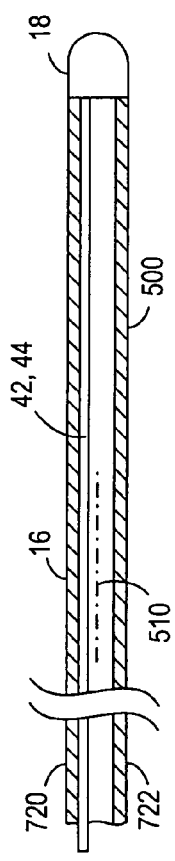
FIG. 11A is a cross-sectional view of a distal portion of the catheter of FIG. 3 in a relaxed position.
Figure 11C:
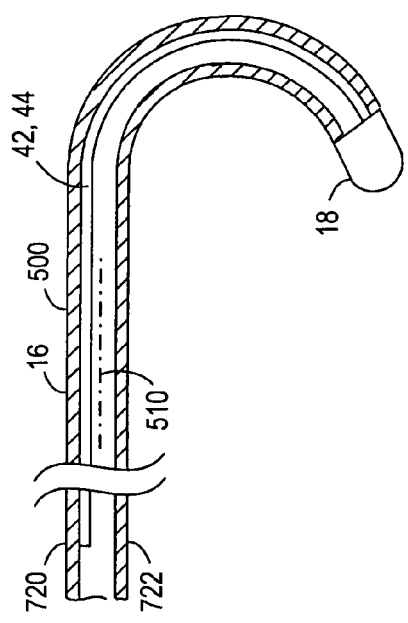
FIG. 11C is a cross-sectional view of a distal portion of the catheter of FIG. 1 steered to the right.

FIG. 11A shows the catheter 12 having a substantially linear configuration. The tubes 42 and 44 are located closer to a first side 720 than a second side 722 within the lumen 506 of the shaft 500. As shown in FIG. 11B, when the electrode assembly 18 is steered towards the first side 520, the first side 520 of the shaft 500 undergoes compression while the second side 522 undergoes tension. Because the tubes 42 and 44 are closer to the compression side of the shaft 500, they are "pushed" proximally relative to the shaft 500. On the other hand, as shown in FIG. 11C, when the electrode assembly 18 is steered towards the second side 522, the second side 522 of the shaft 500 undergoes compression while the first side 520 undergoes tension. Because the tubes 42 and 44 are closer to the tension side of the shaft 500, they are "pulled" distally relative to the shaft 500.

Figure 12:
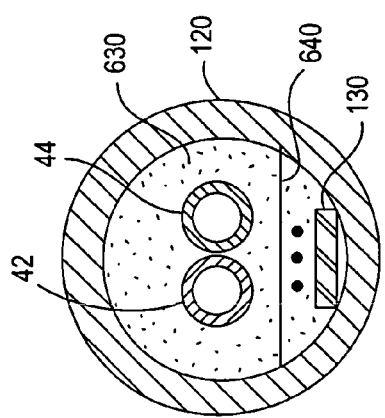
FIG. 12 is a cross-sectional view of an alternative embodiment of the catheter shown in FIG. 1.

The tubes 42 and 44 may move relative to the shaft 500 by as much as 4 to 5 millimeters or more when the electrode assembly 18 is steered. Thus, kinking of the tubes 42 and 44, which may otherwise occur if the axial movement of the tubes 42 and 44 is not accounted for, is prevented when the electrode assembly 18 is steered. In another embodiment, such as that shown in FIG. 12, the tubes 42 and 44 may be located substantially along a center of the guide tube assembly 16 to minimize the axial movement of the tubes 42 and 44 relative to the shaft 500 as the electrode assembly 18 is steered.

Returning to FIG. 3, the guide tube assembly 16 optionally includes a tubular section 730 secured to the interior surface of the shaft 500 and/or the sleeve 536. In one embodiment, the tubular section 730 is located at the junction point 538 which is approximately 2-6 inches from the distal end of the electrode assembly 18. The tubular section 730 may be secured to the interior surface of the shaft 500 at the junction point 538. For example, the tubular section 730 may be secured to the shaft 500 and together with the sleeve 536 at the junction point 538 by a suitable adhesive. Alternatively, the tubular section 730 may be fused together with the shaft 500 and the sleeve 536 at the junction point 538 by a heating or chemical process. Such construction provides additional torsional stiffness at the junction point 538, thereby allowing a torquing force to be transmitted from the handle assembly 14 to the distal portion of the catheter 12, as similarly discussed previously with reference to the sleeve 536. The tubular section 730 has a lumen through which the tubes 42 and 44 extend. The interior surface of the tubular section 730 defining the lumen has a low coefficient of friction, which allows the tubes 42 and 44 of the fluid transfer assembly 40 to slide easily at the junction point 538. The tubular section 730 is preferably made from a polyimide and/or Teflon®. However, other suitable materials may also be used.

A method of using the system 10 will now be described with reference to cardiac ablation therapy. When using the system 10 for cardiac ablation therapy, a physician steers the catheter 12 through a main vein or artery (typically the femoral vein or artery) into the interior region of the heart that is to be treated. The physician then further manipulates the catheter 12 to place the electrode 102 into contact with the tissue within the heart that is targeted for ablation. For example, the physician may operate the steering lever 80 on the handle assembly 14 to steer the electrode assembly, or move (i.e., torque or axially position) the handle assembly 14, for positioning the electrode assembly 18. When the electrode 102 is desirably positioned, radio frequency energy is then directed from the generator 24 to the electrode 102 to ablate the tissue and form a lesion on the contacted tissue.

During the ablation, the cooling assembly 51 is operated to deliver cooled medium to the electrode assembly 18 for cooling of the electrode 102. During closed loop cooling, the medium is circulated back to the discharge reservoir 65 of the cooling assembly 51. Particularly, the cooling assembly 51 supplies the medium through the tube 42 (the delivery tube) into the interior 124 of the electrode assembly 18, while the tube 44 (the discharge tube) returns the medium to the discharge reservoir 65. The flow of cooling liquid through the cavity or interior 124 of the electrode assembly 18 conveys heat away from the thermal mass of the electrode 102 by conductive and convective cooling. In another embodiment, the proximal end 608 of the tube 44 may be coupled to the source reservoir 63, and the medium is circulated back to the source reservoir 63 of the cooling assembly 51.

In closed loop cooling, a pressurized gas could be used as the cooling medium. The pressurized gas would be allowed to expand within the electrode chamber, cooling the electrode by the Joule-Thompson effect. The use of a pressurized gas and the Joule-Thompson effect to cool an electrode is disclosed in Jackson et al. U.S. Pat. No. 5,281,217, which is incorporated herein by reference.

In another embodiment, the system 10 may also be used to perform open loop cooling. In open loop cooling, the electrode assembly 18 has one or more outlet apertures transversely extending through the wall of the tip electrode 102 through which fluid at the interior 124 of the electrode 102 may flow or escape. During open loop cooling, the cooled medium flows into the interior 124 of the electrode assembly 18. The flow of cooling liquid through the interior 124 of the electrode assembly 18 conveys heat away from the thermal mass of the electrode 102 by conductive and convective cooling. The outlet apertures then discharge the medium into the region surrounding the electrode. The discharged medium flows directly into and through the electrode-tissue interface, causing direct cooling of the tissue area being ablated. The direct cooling can reduce the incidence of charring. If the fluid transfer assembly 40 includes tubes 42 and 44, one or both of the tubes 42 and 44 may be used to deliver a cooled medium in open loop cooling. If only one of the tubes 42 and 44 is used for delivery of the medium, the other of the tubes 42 and 44 may be used to carry excess or undelivered medium from the interior 124 of the electrode assembly 18 back to the discharge reservoir 65 or the source reservoir 63. This has the benefit of reducing the head pressure within the electrode assembly 18 and the lumens 604 and 610 of the respective tubes 42 and 44. In another embodiment, the fluid transfer assembly 40 can have a single tube for delivery of the medium. In this case, the tube is coupled to the source reservoir 63, and the cooling assembly 51 does not include the discharge reservoir 65.

Although the system 10 has been described with reference to cardiac ablation therapy, it should be understood that the system 10 may also be used in many different environments and/or applications. For example, the catheter 12 may also be used to deliver drug or a contrast agent. In this case, the fluid transfer assembly 40 functions as a fluid delivery assembly. In one embodiment, if the electrode assembly 18 has one or more openings (such as that for open loop cooling), the catheter 12 may be used for delivery of a medium, such as drug. Such catheter may also be used to remove objects or fluid from a site by applying a suctional force through one or both of the tubes 42 and 44. In this case, instead of coupling the tubes 42 and 44 to the cooling assembly 51, either or both of the tubes 42 and 44 may be coupled to a suction generator, such as a vacuum. If only one of the tubes 42 and 44 is used, the unused tube may be sealed by inserting a plug at the proximal end of the unused tube. Alternatively, the assembly 40 may have only one tube for delivery or suction of a medium or object.

Furthermore, in another embodiment, the electrode assembly 18 may be substituted with another tip assembly that provides a function other than ablation.

Thus, although different embodiments have been shown and described, it would be apparent to those skilled in the art that many changes and modifications may be made thereunto without the departing from the scope of the invention, which is defined by the following claims and their equivalents.

What is claimed is:

1. A catheter, comprising:
   an elongate shaft having an axis, a proximal end and a distal end;
   an operative element carried at the distal end of the shaft, the operative element comprising an interior region;
   a steering mechanism secured to the proximal end of the shaft, wherein the steering mechanism comprises a spring element secured to a distal end of the catheter; and
   a medium conveying conduit carried within the shaft, the conduit having a distal end that is affixed relative to the distal end of the shaft, and a proximal end that is configured to move relative to the proximal end of the shaft, thereby allowing the conduit to slide within the shaft as the shaft is bent, the distal end of the conduit being in fluid communication with the interior region of the operative element.

2. The catheter of claim 1, wherein the operative element comprises an electrode.

3. The catheter of claim 1, wherein the operative element comprises an ablative element.

4. The catheter of claim 3, wherein the ablative element is an ablation electrode.

5. The catheter of claim 1, further comprising a plug mounted to the interior region of the operative element, the plug having a bore in which the distal end of the conduit is mounted.

6. The catheter of claim 5, further comprising a component, wherein the plug includes a cavity in which the component is disposed.

7. The catheter of claim 6, wherein the component is the spring element of the steering mechanism.

8. The catheter of claim 6, wherein the component comprises one or more electrical wires secured to the operative element.

9. The catheter of claim 1, wherein the conduit comprises a hollow tubular element.

10. The catheter of claim 1, wherein the conduit is a liquid conveying conduit.

11. The catheter of claim 1, further comprising another medium conveying conduit carried within the shaft, the other conduit having a distal end that is affixed relative to the distal end of the shaft, and a proximal end that is configured to move relative to the proximal end of the shaft, thereby allowing the other conduit to slide within the shaft as the shaft is bent.

12. The catheter of claim 11, wherein the conduits are secured together.

13. The catheter of claim 11, wherein the conduit and the other conduit are in a side-by-side relationship.

14. The catheter of claim 1, further comprising an internal sleeve secured within the shaft, wherein the conduit is in sliding engagement within the internal sleeve.

15. The catheter of claim 1, wherein the steering mechanism further comprises a steering wire secured to one side of the spring element.

16. The catheter of claim 15, wherein the steering mechanism further comprises an additional steering wire secured to another side of the spring element.

17. The catheter of claim 1, further comprising a handle assembly mounted to the proximal end of the shaft, wherein the handle assembly comprises the steering mechanism, and wherein the proximal end of the conduit slides within the handle assembly.

18. A catheter, comprising:
   an elongate flexible shaft having an axis, a proximal end and a distal end;
   an operative element carried at the distal end of the shaft, the operative element comprising an interior region; and
   a first medium conveying conduit carried within the shaft, the first conduit having a distal end, a proximal end, and a lumen extending between the distal end proximal ends, the lumen having a first cross-sectional size at a first location along the length of the first conduit, and a second different cross-sectional size at a second location along the length of the first conduit, the distal end of the conduit being in fluid communication with the interior region of the operative element; and
   another medium conveying conduit carried within the shaft, the other conduit having a distal end, a proximal end, and a lumen extending between the distal end proximal ends, the lumen having a first cross-sectional size at a first location along the length of the other conduit, and a second different cross-sectional size at a second location along the length of the other conduit.

19. The catheter of claim 18, wherein a major length of the first conduit has a uniform exterior cross-sectional profile.

20. The catheter of claim 18, wherein the conduit comprises a hollow tubular element.

21. The catheter of claim 18, wherein the conduit is a liquid conveying conduit.

22. The catheter of claim 18, wherein the lumen of the first conduit changes from its first cross-sectional size to its second cross-sectional size at a discrete location between the first location and the second location along the length of the first conduit.

23. The catheter of claim 22, wherein the lumen of the first conduit further has a third cross-sectional size at a third location along the length of the first conduit, and the lumen of the first conduit changes from its second cross-sectional size to its third cross-sectional size at a discrete location between the second location and the third location along the length of the first conduit.

24. The catheter of claim 18, wherein the conduits are secured together.

25. The catheter of claim 18, wherein the conduits are in a side-by-side relationship.

26. The catheter of claim 18, further comprising an internal sleeve secured within the shaft, wherein the conduit is in sliding engagement within the internal sleeve.

27. A catheter, comprising:
an elongate flexible shaft having an axis, a proximal end and a distal end;
an operative element carried at the distal end of the shaft, the operative element comprising an interior region;
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element; and
a plug mounted to the interior region of the operative element, the plug having a bore in which the distal end of the conduit is mounted.

28. A catheter, comprising:
an elongate flexible shaft having an axis, a proximal end and a distal end;
an operative element carried at the distal end of the shaft, the operative element comprising an interior region; and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element, wherein the distal end of the conduit is affixed relative to the distal end of the shaft, and the proximal end of the conduit is configured to move relative to the proximal end of the shaft.

29. A catheter, comprising:
an elongate flexible shaft having an axis, a proximal end and a distal end;
an operative element carried at the distal end of the shaft, the operative element comprising an interior region, wherein the operative element comprises one of an electrode and an ablative element; and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element.

30. The catheter of claim 29, wherein the operative element comprises an ablative element.

31. The catheter of claim 30, wherein the ablative element is an ablation electrode.

32. The catheter of claim 29, wherein the operative element comprises an electrode.

33. A catheter, comprising:
an elongate flexible shaft having an axis, a proximal end and a distal end;
an operative element carried at the distal end of the shaft, the operative element comprising an interior region; and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element, wherein the lumen of the conduit has a cross section that varies continuously between the first location and the second location along the length of the conduit.

34. The catheter of claim 33, wherein the lumen of the conduit further has a third cross-sectional size at a third location along the length of the conduit, and the lumen of the conduit has a cross section that varies continuously between the second location and the third location along the length of the conduit.

35. A medical system, comprising:
a) a catheter having
an elongate flexible shaft having an axis, a proximal end and a distal end,
an operative element carried at the distal end of the shaft, the operative element comprising an interior region,
a steering mechanism secured to the proximal end of the shaft, wherein the steering mechanism comprises a spring element secured to a distal end of the catheter, and
a medium conveying conduit carried within the shaft, the conduit having a distal end that is affixed relative to the distal end of the shaft, and a proximal end that is configured to move relative to the proximal end of the shaft, thereby allowing the conduit to slide within the shaft as the shaft is bent, the distal end of the conduit being in fluid communication with the interior region of the operative element; and
b) a pump assembly configured for conveying a medium through the conduit.

36. The system of claim 35, wherein the operative element comprises an electrode.

37. The system of claim 35, further comprising an ablation source, wherein the operative element comprises an ablative element operatively coupled to the ablation source.

38. The system of claim 37, wherein the ablation source is a radio frequency generator, and the ablative element is an ablation electrode.

39. The system of claim 35, wherein the conduit comprises a hollow tubular element.

40. The system of claim 35, wherein the pump assembly is a cooling assembly configured for conveying a cooled medium through the conduit.

41. The system of claim 35, wherein the catheter further comprises another conduit carried within the shaft, the other conduit having a distal end that is affixed relative to the distal end of the shaft, and a proximal end that is configured to move relative to the proximal end of the shaft, thereby allowing the other conduit to slide within the shaft as the shaft is bent, wherein the pump assembly is configured for receiving a medium from the other conduit.

42. The system of claim 41, wherein the conduits are secured together.

43. The system of claim 41, wherein the pump assembly comprises a source reservoir coupled to the proximal end of the conduit, and a discharge reservoir coupled to the proximal end of the other conduit.

44. The system of claim 41, wherein the conduit and the other conduit are in a side-by-side relationship.

45. The system of claim 35, wherein the catheter further has an internal sleeve secured within the shaft, wherein the conduit is in sliding engagement within the internal sleeve.

46. The system of claim 35, wherein the pump assembly comprises a source reservoir coupled to the proximal end of the conduit.

47. The system of claim 35, wherein the catheter further comprises a steering mechanism secured to the proximal end of the shaft.

48. The system of claim 35, wherein the catheter comprises a handle assembly mounted to the proximal end of the shaft, wherein the proximal end of the conduit slides within the handle assembly.

49. A catheter, comprising:
an elongate flexible shaft having an axis, a proximal end and a distal end;
an operative element carried at the distal end of the shaft;
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit; and
a plug secured to the distal end of the conduit, the plug secured relative to a distal portion of the shaft.

50. A catheter, comprising:
an elongate flexible shaft having an axis, a proximal end and a distal end;
an electrode carried at the distal end of the shaft; and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit.

51. The catheter of claim 50, wherein the electrode is an ablation electrode.

52. A catheter, comprising:
an elongate flexible shaft having an axis, a proximal end and a distal end;
an operative element carried at the distal end of the shaft, the operative element comprising an interior region;
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element;
one or more electrical wires secured to the operative element; and
a plug mounted to the interior region of the operative element, the plug having a bore in which the distal end of the conduit is mounted, the plug further having a cavity in which the one or more electrical wires is disposed.

53. A catheter, comprising:
an elongate flexible shaft having an axis, a proximal end and a distal end;
an operative element carried at the distal end of the shaft, the operative element comprising an interior region; and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element, wherein the proximal end of the conduit is configured to move relative to the proximal end of the shaft, thereby allowing the conduit to slide within the shaft as the shaft is bent.

54. The catheter of claim 53, further comprising a handle assembly mounted to the proximal end of the shaft, wherein the proximal end of the conduit slides within the handle assembly.

55. A medical system, comprising:
a) a catheter having
an elongate flexible shaft having an axis, a proximal end and a distal end,
an operative element carried at the distal end of the shaft, the operative element comprising an interior region, wherein the operative element comprises one of an electrode and an ablative element, and
a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element; and
b) a pump assembly configured for conveying a medium through the conduit.

56. The system of claim 55, wherein the operative element comprises an electrode.

57. The system of claim 55, further comprising an ablation source, wherein the operative element comprises an ablative element operatively coupled to the ablation source.

58. The system of claim 57, wherein the ablation source is a radio frequency generator, and the ablative element is an ablation electrode.

59. The system of claim 55, wherein the conduit comprises a hollow tubular element.

60. The system of claim 55, wherein the pump assembly is a cooling assembly configured for conveying a cooled medium through the conduit.

61. The system of claim 55, wherein the pump assembly comprises a source reservoir coupled to the proximal end of the conduit.

62. The system of claim 55, wherein the catheter further comprises a steering mechanism secured to the proximal end of the shaft.

63. A medical system, comprising:
a) a catheter having
  an elongate flexible shaft having an axis, a proximal end and a distal end,
  an operative element carried at the distal end of the shaft, the operative element comprising an interior region,
  a first medium conveying conduit carried within the shaft, the first conduit having a distal end, a proximal end, and a lumen extending between the distal end proximal ends, the lumen having a first cross-sectional size at a first location along the length of the first conduit, and a second different cross-sectional size at a second location along the length of the first conduit, the distal end of the first conduit being in fluid communication with the interior region of the operative element, and
  another medium conveying conduit carried within the shaft, the other conduit having a distal end, a proximal end, and a lumen extending between the distal end proximal ends, the lumen having a first cross-sectional size at a first location along the length of the other conduit, and a second different cross-sectional size at a second location along the length of the other conduit; and
b) a pump assembly configured for conveying a medium through the first conduit.

64. The system of claim 63, wherein the conduits are secured together.

65. The system of claim 63, wherein the pump assembly comprises a source reservoir coupled to the proximal end of the first conduit, and a discharge reservoir coupled to the proximal end of the other conduit.

66. A medical system, comprising:
a) a catheter having
  an elongate flexible shaft having an axis, a proximal end and a distal end,
  an operative element carried at the distal end of the shaft, the operative element comprising an interior region,
  a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element, and
  an internal sleeve secured within the shaft, wherein the conduit is in sliding engagement within the internal sleeve; and
b) a pump assembly configured for conveying a medium through the conduit.

67. A medical system, comprising:
a) a catheter having
  an elongate flexible shaft having an axis, a proximal end and a distal end,
  an operative element carried at the distal end of the shaft, the operative element comprising an interior region,
  a medium conveying conduit carried within the shaft, the conduit having a distal end, a proximal end, and a lumen extending between the distal end proximal ends, the lumen having a first cross-sectional size at a first location along the length of the conduit, and a second different cross-sectional size at a second location along the length of the conduit, the distal end of the conduit being in fluid communication with the interior region of the operative element, and
  a handle assembly mounted to the proximal end of the shaft, wherein the proximal end of the conduit slides within the handle assembly; and
b) a pump assembly configured for conveying a medium through the conduit.

* * * * *